(12) United States Patent
Hoskins et al.

(10) Patent No.: US 6,171,834 B1
(45) Date of Patent: Jan. 9, 2001

(54) **MURI PROTEIN FROM *STREPTOCOCCUS PNEUMONIAE***

(75) Inventors: Jo Ann Hoskins; Franklin Harpold Norris; Pamela Kay Rockey; Paul Robert Rosteck, Jr.; Paul Luther Skatrud, all of Indianapolis; Patti Jean Treadway, Greenwood; Michele Louise Young Bellido; Chyun-Yeh Earnest Wu, both of Indianapolis, all of IN (US)

(73) Assignee: Eli Lilly and Company, Indianapolis, IN (US)

( * ) Notice: Under 35 U.S.C. 154(b), the term of this patent shall be extended for 0 days.

(21) Appl. No.: 09/303,272

(22) Filed: Apr. 30, 1999

Related U.S. Application Data

(62) Division of application No. 08/759,907, filed on Dec. 4, 1996, now Pat. No. 5,948,645.

(51) Int. Cl.[7] .................. C12N 9/00; C12N 9/90; C07K 1/00; C07K 14/00
(52) U.S. Cl. .......... 435/183; 435/233; 530/350; 530/820; 530/825
(58) Field of Search .................. 530/350, 820, 530/825; 435/183, 233

(56) References Cited

U.S. PATENT DOCUMENTS

| | | |
|---|---|---|
| 5,681,694 | 10/1997 | Hoskins et al. . |
| 5,712,108 | 1/1998 | Peery et al. . |
| 5,802,875 | 3/1991 | Lacks et al. . |

OTHER PUBLICATIONS

Doublet, et al., *Biochemistry*, 33:17, pp. 5285–5290, (1994).
Pucci, et al., *J. of Bacteriology*, 176:2, pp. 528–530, (1994).
Baliko G. and Venetianer P., *J. of Bacteriology*, 175:20, pp. 6571–6577, (1993).
Doublet, et al., *J. of Bacteriology*, 174:10, pp. 2970–2979, (1993).
Doublet, et al., *J. of Bacteriology*, 174:18, pp. 5772–5779 (1992).
Yoshimura, et al., *J. of Biological Chemistry*, 268:32, pp. 24242–24246, (Nov. 15, 1993).
Burgess, et al., *J. of Cell Biology*, vol. 111, pp. 2129–2138, (Nov. 1990).
Lazar, et al., *Molecular and Cellular Biology*, pp. 1247–1252, (Mar. 1988).
Gallo, et al., *Biochemistry* , 32:13, pp. 3981–3990, (1993).
Pucci, et al., *J. of Bacteriology*, vol. 177, pp. 336–342, (Jan. 1995).
Nakajima, et al., *Agric. Biol. Chem.*, 52:12, pp. 3099–3104, (1988).
Viering, et al., *J. of Infectious Diseases*, 160:1, pp. 76–82, (Jul. 1989).

*Primary Examiner*—Albert Navarro
(74) *Attorney, Agent, or Firm*—Tina M. Tucker; Thomas D. Webster

(57) ABSTRACT

The invention provides isolated nucleic acid compounds encoding the stem peptide biosynthetic gene murI of *Streptococcus pneumoniae*. Also provided are vectors and transformed heterologous host cells for expressing the MurI enzyme product and a method for identifying compounds that inhibit stem peptide biosynthesis.

1 Claim, 1 Drawing Sheet

MURI PROTEIN FROM *STREPTOCOCCUS PNEUMONIAE*

CROSS-REFERENCE

The present application is a divisional of application Ser. No. 08/759,907, filed Dec. 4, 1996, now U.S. Pat. No. 5,948,645, issued Sep. 7, 1999.

BACKGROUND OF THE INVENTION

This invention relates to recombinant DNA technology. In particular the invention pertains to the cloning of the murI gene encoding glutamate racemase of *Streptococcus pneumoniae* and the use of the murI gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in *Streptococcus pneumoniae* which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that compounds that interfere with cell wall biosynthesis have low toxicity in humans and potentially high therapeutic value.

The bacterial cell wall structure contains a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide," or "Park nucleotide") containing alternating D and L amino acid residues. The nascent peptidoglycan layer is stabilized by an enzymatic step which crosslinks adjacent pentapeptide moieties. Without this crosslinking step the peptidoglycan structure is severely weakened and susceptible to degradation. Indeed, it is the peptidoglycan crosslinking step that has been a frequently targeted site for antibiotic compounds such as the beta-lactam antibiotics.

Unlike the peptidoglycan crosslinking step, the stem peptide pathway has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by UDP-N-acetylmuramate:L-alanine ligase; UDP-N-acetyl-muramyl-L-alanine:D-glutamate ligase; UDP-N-acetyl-muramyl-L-alanyl-D-isoglutamate:L-lysine ligase; UDP-N-acetylmuramyl-L-alanyl-D-isoglutamyl-L-lysine:D-alanyl-D-alanine ligase; and D-alanyl-D-alanine ligase, the final product, UDPMurNAc-L-Ala-D-isoGlu-L-lysine-D-Ala-D-Ala, is produced in *Streptococcus pneumoniae*.

The enzymatic steps involved in the formation of the stem peptide are potential targets for new antibacterial agents. A few inhibitors, which target this pathway, have been developed. For example, D-cycloserine inhibits alanine racemase and D-alanine-D-alanine ligase; phosphonomycin inhibits the conversion of UDP-GlcNAc to UDP-GlcNac-enolpyruvate; and Alafosfalin inhibits the formation of UDP-MurNac-L-Ala.

While inroads in the development of new antibiotics and new targets for antibiotic compounds have emerged in a variety of microorganisms, progress has been less apparent in *Streptococcus pneumoniae*. In part, *Streptococcus pneumoniae* presents a special case because this organism is highly mutagenic and readily takes up and integrates exogenous foreign DNA from its surroundings, thereby increasing the possibility of acquiring or creating novel genes. Thus, the need for new antibacterial compounds and new targets for antibacterial therapy is especially acute in *Streptococcus pneumoniae*.

SUMMARY OF THE INVENTION

The present invention is designed to meet the aforementioned need and provides, inter alia, isolated nucleic acid molecules that encode the murI gene product from *Streptococcus pneumoniae*. The invention also provides the protein product of the *Streptococcus pneumoniae* murI gene, glutamate racemase (MurI protein), in substantially purified form.

Having the cloned murI gene of *Streptococcus pneumoniae* enables the production of recombinant MurI protein and the implementation of large scale screens to identify new inhibitory compounds targeted at the stem peptide biosynthetic pathway. It may be possible to combine stem peptide biosynthetic enzymes in a single screen to examine several steps at the same time. Structural analysis of the MurI protein will enable structure-based drug design to develop novel compounds effective in the treatment of antibiotic resistant microorganisms.

In one embodiment the present invention relates to an isolated DNA molecule encoding MurI protein, said DNA molecule comprising the nucleotide sequence identified as SEQ ID NO. 1:

In another embodiment the present invention relates to a MurI protein molecule, wherein said protein molecule comprises the sequence identified as SEQ ID NO. 2.

In a further embodiment the present invention relates to a ribonucleic acid molecule encoding MurI protein, said ribonucleic acid molecule comprising the sequence identified as SEQ ID NO. 3:

In yet another embodiment, the present invention relates to a recombinant DNA vector which incorporates the *Streptococcus pneumoniae* murI gene in operable linkage to gene expression sequences enabling the murI gene to be transcribed and translated in a host cell.

In still another embodiment the present invention relates to homologous or heterologous host cells which have been transformed or transfected with the cloned murI gene of *Streptococcus pneumoniae* such that the murI gene is expressed in the host cell.

In a still further embodiment, the present invention relates to a method for identifying compounds that inhibit the enzymatic activity of the MurI protein of *Streptococcus pneumoniae*.

DESCRIPTION OF THE DRAWING

FIGURE. Plasmid pPSJ324, useful for high level expression of the *Streptococcus pneumoniae* murI gene in the heterologous procaryotic host cell *Eschericia coli*.

DEFINITIONS

Figure 1:
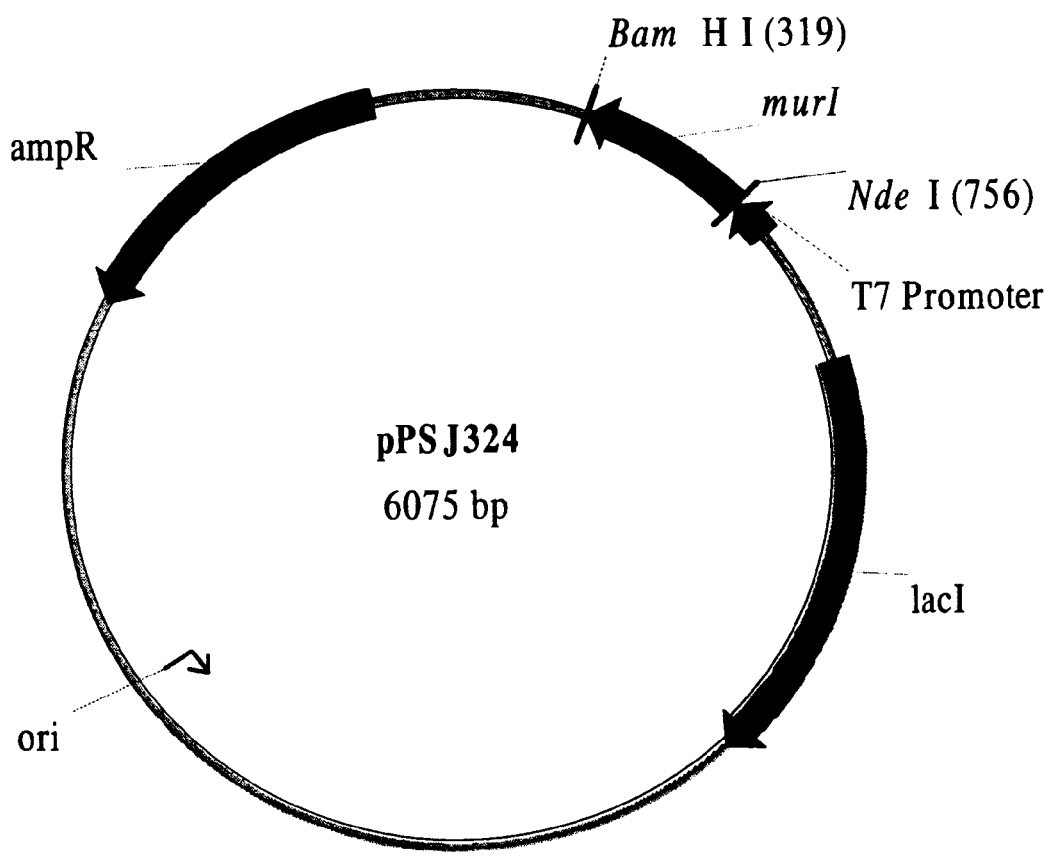

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"MurI" refers to the protein encoded by murI, glutamate racemase.

"MurD" refers to the enzyme UDPNAc muramyl-L-alanyl-D-isoglutamate ligase.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

DETAILED DESCRIPTION

The murI gene of *Streptococcus pneumoniae* encodes an enzyme which catalyzes the conversion of L-glutamic acid to D-glutamic acid. The stem peptide pathway is necessary for the synthesis of the peptidoglycan layer, which is an essential part of the bacterial cell wall. There are at least 10 enzymes involved in stem peptide biosynthesis, including L-glutamic acid recemase (SEQ ID NO. 2), encoded by the murI gene (SEQ ID NO.1).

The murI gene of *Streptococcus pneumoniae* comprises a DNA sequence of 792 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recogize that the murI gene may be obtained by a plurality of applicable genetic and recombinant DNA techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the murI gene of *Streptococcus pneumoniae* or fragment thereof could be isolated by PCR amplification of *Streptococcus pneumoniae* genomic DNA or cDNA using oligonucleotide primers targeted to any suitable region of SEQ ID NO. 1. Methods for PCR amplification are widely known in the art. See e.g. *PCR Protocols: A Guide to Method and Application,* Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One embodiment of the present invention relates to the substantially purified protein encoded by the murI gene, or a fragment of said protein, or modification thereof, or a functionally related protein of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, N.Y., 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl ben-zhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celsius or below, preferably –20° C. for thirty minutes followed by thirty minutes at 0° C.

The protein of the present invention can also be produced by recombinant DNA methods using the cloned murI gene of *Streptococcus pneumoniae*. Recombinant methods are preferred if a high yield is desired. Expression of the cloned murI gene can be carried out in a variety of suitable host cells well known to those skilled in the art. The murI gene is introduced into a host cell by any suitable means, well known to those skilled in the art. While chromosomal integration of the cloned murI gene is within the scope of the present invention, it is preferred that the gene be cloned into a suitable extra-chromosomally maintained expression vector so that the coding region of the murI gene is operably linked to a constitutive or inducible promoter.

The basic steps in the recombinant production of the MurI protein are:

a) constructing a natural, synthetic or semi-synthetic DNA encoding MurI protein;

b) integrating said DNA into an expression vector in a manner suitable for expressing the MurI protein, either alone or as a fusion protein;

c) transforming or otherwise introducing said vector into an appropriate eucaryotic or procaryotic host cell forming a recombinant host cell, d) culturing said recombinant host cell in a manner to express the MurI protein; and e) recovering and substantially purifying the MurI protein by any suitable means, well known to those skilled in the art.

Expressing Recombinant MurI Protein in Procaryotic and Eucaryotic Host Cells

In general, procaryotes are used for cloning DNA sequences and for constructing the vectors of the present invention. Procaryotes may also be employed in the production of the MurI protein. For example, the *Escherichia coli* K12 strain 294 (ATCC No. 31446) is particularly useful for the procaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomryces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to procaryotes, a variety of mammalian cell systems and eucaryotic microorganisms such as yeast are suitable host cells. The yeast *Saccharomyces cerevisiae* is the most commonly used eucaryotic microorganism. A number of other yeasts such as *Kluyveromyces lactis* are also suitable. For expression in Saccharomnyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced MurI Protein

An expression vector carrying the cloned murI gene of *Streptococcus pneumoniae* is transformed or transfected into a suitable host cell using standard methods. Cells which contain the vector are then propagated under conditions suitable for expression of the MurI protein. If the gene is under the control of an inducible promoter then suitable growth conditions would incorporate the appropriate inducer. The recombinantly-produced protein may be purified from cellular extracts of transformed cells by any suitable means.

In a preferred process for protein purification the murI gene is modified at the 5' end to incorporate several histidine residues at the amino terminus of the MurI protein product. This "histidine tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure MurI protein starting from a crude cellular extract. Moreover, the his-tag can be constructed to contain a Factor Xa cleavage site so that the tag can be removed if necessary to regenerate the native protein.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one codon due to the degeneracy of the genetic code. Because these alternative nucleic acid sequences would encode the same amino acid sequences, the present invention further comprises these alternate nucleic acid sequences.

The murI gene, which comprises nucleic acid encoding SEQ ID NO:2, may be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the murI gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

In an alternative methodology, namely PCR, the murI DNA sequence comprising a portion or all of SEQ ID NO:1 can be generated from *Streptococcus pneumoniae* genomic DNA using suitable oligonucleotide primers complementary to SEQ ID NO:1 or region therein, as described in U.S. Pat. No. 4,889,818, which hereby is incorporated by reference. Suitable protocols for performing the PCR are disclosed in, for example, *PCR Protocols: A Guide to Method and Applications*, Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a murI DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques including, for example, hybridization screens of genomic or subgenomic libraries. A nucleic acid compound comprising SEQ ID NO:1, SEQ ID NO:3 or a complementary sequence thereof, or a fragment thereof, and which is at least 18 base pairs in length, and which will selectively hybridize to *Streptococcus pneumoniae* DNA or mRNA encoding murI, is provided. Preferably, the 18 or more base pair compound is DNA. A probe or primer length of at least 18 base pairs is dictated by theoretical and practical considerations. See e.g. B. Wallace and G. Miyada, "Oligonucleotide Probes for the Screening of Recombinant DNA Libraries," In *Methods in Enzymology*, Vol. 152, 432–442, Academic Press (1987).

These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1 . Plasmid pPSJ324 is an especially preferred DNA vector of the present invention.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the resent invention comprise RNA viruses, DNA viruses, lytic acteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters which respond to a variety of inducers, for example, carbon source, metal ions, heat, etc. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. The preferred host cell is any strain of *E. coli* which can accomodate high level expression of an exogenously introduced gene. Preferred vectors for expression are those which comprise SEQ ID NO:1. An especially preferred expression vector for use in *E. coli* is plasmid pPSJ324, which comprises SEQ ID NO:1. (See Figure).

Transformed host cells may be cultured under conditions well known to skilled artisans such that SEQ ID NO:2 is expressed, thereby producing MurI protein in the recombinant host cell.

For the purpose of identifying or developing inhibitors of the stem peptide pathway, it would be desirable to determine those agents which inhibit the MurI step. A method for determining whether a substance will inhibit the enzymatic reaction catalyzed by the MurI protein comprises contacting the MurI protein with a test inhibitory compound and monitoring MurI enzyme activity by any suitable means.

The instant invention provides such a screening system useful for discovering compounds which inhibit the MurI protein, said screening system comprising the steps of:

a) preparing MurI enzyme;

b) exposing said MurI enzyme to a test inhibitor;

c) introducing a specific MurI substrate; and d) quantifying the loss of activity of said MurI enzyme.

Utilization of the screening system described above provides a means to determine compounds which interfere with stem peptide biosynthesis. This screening method may be adapted to automated procedures such as a PANDEX® (Baxter-Dade Diagnostics) system, allowing for efficient high-volume screening of potential therapeutic agents.

In such a screening protocol MurI enzyme is prepared as described herein, preferably using recombinant DNA technology. A test inhibitory compound is then introduced into the reaction vessel containing the MurI enzyme, followed by addition of enzyme substrate. Alternatively, substrate may be added simultaneously with the test compound. For example, in a preferred method radioactively or chemically-labeled substrate may be used. The products of the enzymatic reaction are assayed for the chemical label or radioactivity by any suitable means. The absence or diminution of the chemical label or radioactivity indicates the degree to which the reaction is inhibited.

Skilled artisans will recognize that $IC_{50}$ values are dependent on the selectivity of the compound tested. For example, a compound with an $IC_{50}$ which is less than 10 nM is generally considered an excellent candidate for drug therapy. However, a compound which has a lower affinity, but is selective for a particular target, may be an even better candidate. The skilled artisan will recognize that any information regarding inhibitory activity or selectivity of a particular compound is beneficial in the pharmaceutical arts.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Streptococcus pnuemoniae* murI Gene in a Homologous or Heterologous Host Plasmid pPSJ324 (See FIGURE) is an approximately 6075 base pair expression vector suitable for expressing the murI gene of *S. pneumoniae* in the procaryotic host *E. coli*. This plasmid contains an origin of replication (Ori), an ampicillin resistance gene (Amp), useful for selecting cells which have incorporated the vector following a tranformation procedure, and further comprises the lacI gene for repression of the lac operon, as well as the T7 promoter and T7 terminator sequences in operable linkage to the coding region of the murI gene. Parent plasmid pET11A (obtained from Novogen, Madison, Wis.) was linearized by digestion with endonucleases NdeI and BamHI. Linearized pET11A was ligated to a DNA fragment bearing NdeI and BamHI sticky ends and further comprising the coding region of the *S. pneumoniae* murI gene.

The murI gene, which was ligated into pPSJ324, was modified at the 5' end (amino terminus of encoded protein) in order to simplify purification of the encoded MurI protein product. For this purpose, an oligonucleotide encoding 8 histidine residues and a factor Xa cleavage site was inserted after the ATG start codon at nucleotide positions 1 to 3 of SEQ ID NO: 1. Placement of the histidine residues at the amino terminus of the encoded protein serves only to enable the IMAC one-step protein purification procedure (See below). If necessary the histidine residues can be cleaved off using factor Xa to regenerate the native protein.

EXAMPLE 2

Expression of *Streptococcus pneumoniae* murI Gene in *Echerichia coli* and Purification of MurI Enzyme Plasmid pPSJ324 is transformed into *E. coli* BL21 (DE3) (hsdS gal λcIts857 ind1Sam7nin5lacUV5-T7gene 1) using standard methods (See e.g. Sambrook et al. Supra). Transformants, selected for resistance to ampicillin, are chosen at random and tested for the presence of pPSJ324 by agarose gel electrophoresis using quick plasmid preparations. Id. Colonies that contain pPSJ324 are grown, processed, and the protein product encoded by the murI gene purified by immobilized metal ion affinity chromatography (IMAC), essentially as described in U.S. Pat. No. 4,569,794, the entire contents of which is hereby incorporated by reference.

Briefly, the IMAC column is prepared as follows. A metal-free chelating resin (e.g. SEPHAROSE 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract prepared from a recombinant host transformed or transfected with plasmid pPSJ324.

After washing the column with a suitable buffer, pH 7.5 to remove unbound proteins and other materials, the bound recombinant MurI protein is eluted in a buffer at pH 4.3, essentially as described in U.S. Pat. No. 4,569,794.

EXAMPLE 3

Biochemical Assay for Inhibitors of *Streptococcus pneumoniae* MurI Enzyme Product The activity of the MurI enzyme is assayed by monitoring the formation of UDP-MurNAc-L-Ala-D-Glu in a coupled reaction with MurD enzyme. The enzyme reaction substrate composition consists of 0.1M Tris/HCl pH 8.6, 20 mM $MgCl_2$, 5 mM ATP, 100 µl M UDP-MurNAc-L-Ala, 50 µM L-glutamic acid, and enzyme MurD in a final volume of 50 µl. MurI enzyme is added to initiate the reaction or MurI enzyme may be added together with the other substrate components. Substrate UDP-MurNAc-L-Ala is purified as described in B. Flouret et al., Reverse-phase high-pressure liquid chromatography of uridine diphosphate N-Acetylmuramyl peptide precursors of bacterial cell wall peptidoalycan, Anal. Biochem. 114, 59–63 (1981). The reaction is incubated for 30 min at 37° C., and terminated by the addition of 10 µl of glacial acetic acid. The amount of product generated is determined by HPLC, essentially as described in Flouret et. al. (Id.). Briefly, the nucleotide precursors are extracted in the cold with trichloroacetic acid and purified by gel filtration on fine SEPHADEX G-25. The UDP-MurNac derivatives are eluted with water in a volume slightly larger than the exclusion volume of the column. Separation and further purification of UDP-MurNAc derivatives are carried out by ion-exchange chromatography on Dowex AG1x 2 (200–400 mesh) according to the method of Park & Chatterjee, *Methods in Enzymology,* 8, 466–472 (Academic Press, N.Y. 1966). HPLC analyses are performed with a Waters Associates apparatus consisting of two Model 6000 A solvent delivering systems, a Model 660 solvent programmer, and a Model 450 variable wavelength detector which monitors the eluant at 220 nm or at 262 nm. Peaks are recorded and integrated with a Spectra Physics SP 4100 model computing integrator (Spectra Physics, Santa Clara, Calif.).

Inhibition studies are carried out using the reaction conditions described in the preceding paragraph. Test inhibitory compounds are added to a final concentration of between 1 mM and 10 mM, and the percentage inhibition ascertained by comparison with a control in which no test inhibitor is present.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 792 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..792

(xi) SEQUENCE DESCRIPTION: SEQ ID NO:1:

```
ATG GAT AAT CGA CCA ATT GGT TTT TTG GAT TCG GGT GTC GGG GGC TTG      48
Met Asp Asn Arg Pro Ile Gly Phe Leu Asp Ser Gly Val Gly Gly Leu
 1               5                  10                  15

ACC GTT GTG CGC GAG CTC ATG CGC CAG CTT CCC CAT GAA GAA ATC GTC      96
Thr Val Val Arg Glu Leu Met Arg Gln Leu Pro His Glu Glu Ile Val
             20                  25                  30

TAT ATT GGA GAT TCG GCG CGG GCG CCC TAT GGC CCC CGT CCT GCT GAG     144
Tyr Ile Gly Asp Ser Ala Arg Ala Pro Tyr Gly Pro Arg Pro Ala Glu
         35                  40                  45

CAA ATT CGT GAA TAT ACT TGG CAG CTG GTC AAC TTT CTC TTG ACC AAG     192
Gln Ile Arg Glu Tyr Thr Trp Gln Leu Val Asn Phe Leu Leu Thr Lys
     50                  55                  60

GAT GTC AAA ATG ATT GTC ATT GCT TGT AAC ACT GCG ACT GCG GTT GTC     240
Asp Val Lys Met Ile Val Ile Ala Cys Asn Thr Ala Thr Ala Val Val
 65                  70                  75                  80

TGG GAA GAA ATC AAG GCT CAA CTA GAT ATT CCT GTC TTG GGT GTA ATT     288
Trp Glu Glu Ile Lys Ala Gln Leu Asp Ile Pro Val Leu Gly Val Ile
                 85                  90                  95

TTG CCA GGA GCT TCG GCA GCC ATC AAG TCC AGT CAA GGT GGG AAA ATC     336
Leu Pro Gly Ala Ser Ala Ala Ile Lys Ser Ser Gln Gly Gly Lys Ile
            100                 105                 110

GGA GTG ATT GGA ACG CCC ATG ACG GTA CAA TCA GAC ATA TAC CGT CAG     384
Gly Val Ile Gly Thr Pro Met Thr Val Gln Ser Asp Ile Tyr Arg Gln
        115                 120                 125

AAA ATC CAT GAT CTG GAT CCC GAC TTA CAG GTG GAG AGC TTG GCC TGT     432
Lys Ile His Asp Leu Asp Pro Asp Leu Gln Val Glu Ser Leu Ala Cys
    130                 135                 140
```

-continued

```
CCC AAG TTT GCT CCC TTG GTT GAG TCA GGT GCC CTG TCA ACC AGT GTT    480
Pro Lys Phe Ala Pro Leu Val Glu Ser Gly Ala Leu Ser Thr Ser Val
145                 150                 155                 160

ACC AAG AAG GTG GTC TAT GAA ACC CTG CGT CCC TTG GTT GGA AAG GTG    528
Thr Lys Lys Val Val Tyr Glu Thr Leu Arg Pro Leu Val Gly Lys Val
                165                 170                 175

GAT AGC CTG ATT TTG GGC TGT ACT CAT TAT CCA CTC CTT CGC CCT ATT    576
Asp Ser Leu Ile Leu Gly Cys Thr His Tyr Pro Leu Leu Arg Pro Ile
            180                 185                 190

ATC CAA AAT GTG ATG GGG CCA AAG GTT CAG CTC ATC GAT AGT GGG GCA    624
Ile Gln Asn Val Met Gly Pro Lys Val Gln Leu Ile Asp Ser Gly Ala
        195                 200                 205

GAG TGC GTA CGG GAT ATT TCA GTC TTA CTC AAT TAT TTT GAA ATC AAT    672
Glu Cys Val Arg Asp Ile Ser Val Leu Leu Asn Tyr Phe Glu Ile Asn
    210                 215                 220

CGT GGT CGC GAT GCT GGA CCA CTC CAT CAC CGT TTT TAC ACA ACA GCC    720
Arg Gly Arg Asp Ala Gly Pro Leu His His Arg Phe Tyr Thr Thr Ala
225                 230                 235                 240

AGT AGC CAA AGT TTT GCA CAA ATT GGT GAA GAA TGG CTG GAA AAA GAG    768
Ser Ser Gln Ser Phe Ala Gln Ile Gly Glu Glu Trp Leu Glu Lys Glu
                245                 250                 255

ATT CAT GTG GAG CAT GTA GAA TTA                                    792
Ile His Val Glu His Val Glu Leu
            260
```

(2) INFORMATION FOR SEQ ID NO:2:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Asn Arg Pro Ile Gly Phe Leu Asp Ser Gly Val Gly Leu
 1               5                  10                  15

Thr Val Val Arg Glu Leu Met Arg Gln Leu Pro His Glu Glu Ile Val
                20                  25                  30

Tyr Ile Gly Asp Ser Ala Arg Ala Pro Tyr Gly Pro Arg Pro Ala Glu
            35                  40                  45

Gln Ile Arg Glu Tyr Thr Trp Gln Leu Val Asn Phe Leu Leu Thr Lys
        50                  55                  60

Asp Val Lys Met Ile Val Ile Ala Cys Asn Thr Ala Thr Ala Val Val
65                  70                  75                  80

Trp Glu Glu Ile Lys Ala Gln Leu Asp Ile Pro Val Leu Gly Val Ile
                85                  90                  95

Leu Pro Gly Ala Ser Ala Ala Ile Lys Ser Ser Gln Gly Gly Lys Ile
            100                 105                 110

Gly Val Ile Gly Thr Pro Met Thr Val Gln Ser Asp Ile Tyr Arg Gln
        115                 120                 125

Lys Ile His Asp Leu Asp Pro Asp Leu Gln Val Glu Ser Leu Ala Cys
    130                 135                 140

Pro Lys Phe Ala Pro Leu Val Glu Ser Gly Ala Leu Ser Thr Ser Val
145                 150                 155                 160

Thr Lys Lys Val Val Tyr Glu Thr Leu Arg Pro Leu Val Gly Lys Val
                165                 170                 175

Asp Ser Leu Ile Leu Gly Cys Thr His Tyr Pro Leu Leu Arg Pro Ile
            180                 185                 190
```

Ile Gln Asn Val Met Gly Pro Lys Val Gln Leu Ile Asp Ser Gly Ala
        195                 200                 205

Glu Cys Val Arg Asp Ile Ser Val Leu Leu Asn Tyr Phe Glu Ile Asn
        210                 215                 220

Arg Gly Arg Asp Ala Gly Pro Leu His His Arg Phe Tyr Thr Thr Ala
225                 230                 235                 240

Ser Ser Gln Ser Phe Ala Gln Ile Gly Glu Glu Trp Leu Glu Lys Glu
            245                 250                 255

Ile His Val Glu His Val Glu Leu
            260

(2) INFORMATION FOR SEQ ID NO:3:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

```
AUGGAUAAUC GACCAAUUGG UUUUUUGGAU UCGGGUGUCG GGGGCUUGAC CGUUGUGCGC      60

GAGCUCAUGC GCCAGCUUCC CCAUGAAGAA AUCGUCUAUA UUGGAGAUUC GGCGCGGGCG     120

CCCUAUGGCC CCCGUCCUGC UGAGCAAAUU CGUGAAUAUA CUUGGCAGCU GGUCAACUUU     180

CUCUUGACCA AGGAUGUCAA AAUGAUUGUC AUUGCUUGUA ACACUGCGAC UGCGGUUGUC     240

UGGGAAGAAA UCAAGGCUCA ACUAGAUAUU CCUGUCUUGG GUGUAAUUUU GCCAGGAGCU     300

UCGGCAGCCA UCAAGUCCAG UCAAGGUGGG AAAAUCGGAG UGAUUGGAAC GCCCAUGACG     360

GUACAAUCAG ACAUAUACCG UCAGAAAAUC CAUGAUCUGG AUCCCGACUU ACAGGUGGAG     420

AGCUUGGCCU GUCCCAAGUU UGCUCCCUUG GUUGAGUCAG GUGCCCUGUC AACCAGUGUU     480

ACCAAGAAGG UGGUCUAUGA AACCCUGCGU CCCUUGGUUG GAAAGGUGGA UAGCCUGAUU     540

UUGGGCUGUA CUCAUUAUCC ACUCCUUCGC CCUAUUAUCC AAAAUGUGAU GGGGCCAAAG     600

GUUCAGCUCA UCGAUAGUGG GGCAGAGUGC GUACGGGAUA UUUCAGUCUU ACUCAAUUAU     660

UUUGAAAUCA AUCGUGGUCG CGAUGCUGGA CCACUCCAUC ACCGUUUUUA CACAACAGCC     720

AGUAGCCAAA GUUUUGCACA AAUUGGUGAA GAAUGGCUGG AAAAAGAGAU UCAUGUGGAG     780

CAUGUAGAAU UA                                                        792
```

We claim:

1. An isolated MurI protein from *Streptococcus pneumoniae* having the amino acid sequence:

Met Asp Asn Arg Pro Ile Gly Phe Leu Asp Ser
1               5                   10

Gly Val Gly Gly Leu Thr Val Val Arg Glu Leu
                15                  20

Met Arg Gln Leu Pro His Glu Glu Ile Val Tyr
        25                  30

Ile Gly Asp Ser Ala Arg Ala Pro Tyr Gly Pro
        35                  40

Arg Pro Ala Glu Gln Ile Arg Glu Tyr Thr Trp
        45                  50                  55

Gln Leu Val Asn Phe Leu Leu Thr Lys Asp Val
                60                  65

Lys Met Ile Val Ile Ala Cys Asn Thr Ala Thr
                70                  75

Ala Val Val Trp Glu Glu Ile Lys Ala Gln Leu
                80                  85

-continued

```
Asp Ile Pro Val Leu Gly Val Ile Leu Pro Gly
         90                  95
Ala Ser Ala Ala Ile Lys Ser Ser Gln Gly Gly
100              105                 110
Lys Ile Gly Val Ile Gly Thr Pro Met Thr Val
             115                 120
Gln Ser Asp Ile Tyr Arg Gln Lys Ile His Asp
                 125             130
Leu Asp Pro Asp Leu Gln Val Glu Ser Leu Ala
         135                 140
Cys Pro Lys Phe Ala Pro Leu Val Glu Ser Gly
         145                 150
Ala Leu Ser Thr Ser Val Thr Lys Lys Val Val
155              160                 165
Tyr Glu Thr Leu Arg Pro Leu Val Gly Lys Val
                 170             175
```

-continued

```
Asp Ser Leu Ile Leu Gly Cys Thr His Tyr Pro
                 180             185
Leu Leu Arg Pro Ile Ile Gln Asn Val Met Gly
                 190             195
Pro Lys Val Gln Leu Ile Asp Ser Gly Ala Glu
             200                 205
Cys Val Arg Asp Ile Ser Val Leu Leu Asn Tyr
210              215                 220
Phe Glu Ile Asn Arg Gly Arg Asp Ala Gly Pro
                 225                 230
Leu His His Arg Phe Tyr Thr Thr Ala Ser Ser
                 235             240
Gln Ser Phe Ala Gln Ile Gly Glu Glu Trp Leu
             245             250
Glu Lys Glu Ile His Val Glu His Val Glu Leu
255              260
```

* * * * *